(12) United States Patent
Chatzou et al.

(10) Patent No.: US 11,657,898 B2
(45) Date of Patent: May 23, 2023

(54) BIOLOGICAL INTERACTION AND DISEASE TARGET PREDICTIONS FOR COMPOUNDS

(71) Applicant: LIFEBIT BIOTECH LIMITED, London (GB)

(72) Inventors: Maria Chatzou, London (GB); Pablo Preto Barja, London (GB); Niklas Henrik Benjamin Kokkola, London (GB); Rishabh Shukla, London (GB)

(73) Assignee: LIFEBIT BIOTECH LIMITED

( * ) Notice: Subject to any disclaimer, the term of this patent is extended or adjusted under 35 U.S.C. 154(b) by 0 days.

(21) Appl. No.: 17/167,944

(22) Filed: Feb. 4, 2021

(65) Prior Publication Data

US 2021/0158897 A1 May 27, 2021

Related U.S. Application Data

(63) Continuation of application No. PCT/EP2020/059686, filed on Apr. 3, 2020.

(30) Foreign Application Priority Data

Apr. 5, 2019 (GB) ..................... 1904887

(51) Int. Cl.
*G16B 25/10* (2019.01)
*G16B 40/30* (2019.01)
*G16B 5/20* (2019.01)
*G16B 40/20* (2019.01)

(52) U.S. Cl.
CPC .............. *G16B 25/10* (2019.02); *G16B 5/20* (2019.02); *G16B 40/20* (2019.02); *G16B 40/30* (2019.02)

(58) Field of Classification Search
None
See application file for complete search history.

(56) References Cited

U.S. PATENT DOCUMENTS

2017/0277826 A1 9/2017 Ozerov et al.
2019/0034581 A1 1/2019 Aliper et al.

FOREIGN PATENT DOCUMENTS

WO 2017122785 A1 7/2017
WO 2019231624 A2 12/2019

OTHER PUBLICATIONS

Artursson, Per, and J. Karlsson. "Correlation between oral drug absorption in humans and apparent drug permeability coefficients in human intestinal epithelial (Caco-2) cells." Biochemical and biophysical research communications 175.3 (1991): 880-885.*
Wessel, Matthew D., et al. "Prediction of human intestinal absorption of drug compounds from molecular structure." Journal of Chemical Information and Computer Sciences 38.4 (1998): 726-735.*
Brinks, Vera, et al. "Preclinical models used for immunogenicity prediction of therapeutic proteins." Pharmaceutical research 30.7 (2013): 1719-1728.*
Goodfellow, Ian, et al. "Generative adversarial nets." Advances in neural information processing systems 27 (2014).*
Purushotham, Sanjay, et al. "Variational recurrent adversarial deep domain adaptation." (2016).*
International Search Report and Written Opinion issued in International Patent Application No. PCT/EP2020/059686 dated Jun. 30, 2020 (18 pages).
Written Opinion issued in International Patent Application No. PCT/EP2020/059686 dated Nov. 27, 2020 (9 pages).
Jannis Born, "Reinforcement learning-driven de-novo design of anticancer compounds conditioned on biomolecular profiles", Cornell University Library, 201 Olin Library Cornell University Ithaca, NY 14853, Aug. 29, 2019, arxiv.org (12 pages).
Artur Kadurin et al., "The cornucopia of meaningful leads: Applying deep adversarial autoencoders for new molecule development in oncology", Oncotarget, 2017, 8(7): 10883-10890 (8 pages).
Oscar Mendez-Lucio, "De novo generation of hit-like molecules from gene expression signatures using artificial intelligence", Nature Communications, 2020, 11(10): pp. 1-10 (10 pages).
Kang Yang et al., "Prediction of DTIs for high-dimensional and class-imbalanced data based on CGAN", 2018 IEEE International Conference on Bioinformatics and Biomedicine (BIBM), Dec. 3, 2018, pp. 788-791 (4 pages).

* cited by examiner

*Primary Examiner* — G Steven Vanni
(74) *Attorney, Agent, or Firm* — Dorsey & Whitney LLP

(57) ABSTRACT

The present disclosure provides for generation of predictions for a compound based on input data corresponding to the compound. A cell digital twin receives the input data corresponding to the compound and generates predictions based on the input data. The cell digital twin comprises a prediction engine including a model generated using reduced representations of known cell response profiles corresponding to tested compounds. The model is updated by a feedback loop between a validation engine of the cell digital twin and the model.

18 Claims, 8 Drawing Sheets

BIOLOGICAL INTERACTION AND DISEASE TARGET PREDICTIONS FOR COMPOUNDS

CROSS-REFERENCE TO RELATED APPLICATIONS

This application is a continuation of International Application No. PCT/EP2020/059686, filed Apr. 3, 2020, entitled "BIOACTIVE COMPOUND EFFECT AND DISEASE TARGET PREDICTIONS," which claims the benefit of the earlier filing date of United Kingdom Application Number 1904887.5 filed Apr. 5, 2019, the entire contents of each of which are hereby incorporated by reference in their entirety for any purpose.

BACKGROUND

Ascertaining a mode of action, target, target disease, immune response, or other information about a bioactive compound from cell response data is difficult, time consuming, and resource intensive, as it requires many laboratory experiments and research hours. Further, manual analysis of this data may not identify significant correlations between the bioactive compounds at hand, their effect, and other well-known bioactive compounds.

SUMMARY

Example methods are described herein. Some example methods include receiving, at a cell digital twin, input data corresponding to a compound of interest and generating, by the cell digital twin, validated predictions based on the input data, where the cell digital twin comprises a prediction engine comprising a generative neural network generated using known cell response profiles corresponding to tested compounds. The prediction engine may be configured to generate predictions using the generative neural network and the prediction engine may be updated by a feedback loop between a validation engine of the cell digital twin and the prediction engine, Some example methods may further include generating a cell response profile based on the input data and generating a reduced cell response profile using the generative neural network.

Some example methods may further include generating validation information from the predictions using the validation engine configured to extract information related to the predictions from one or more reference sources, where the validated predictions are a combination of the predictions and the validation information.

Some example methods may further include updating the prediction engine using the validation information.

In some examples, the cell response profile comprises genetic expression data and peptide and protein levels and types.

In some examples, the generative neural network includes reduced known cell response profiles.

In some examples, the predictions include one or more of predicted immune response, predicted immune coverage, predicted mode of action, or predicted target diseases.

In some examples, the prediction engine comprises an immune response model configured to generate the predicted immune response and the predicted immune coverage and a drug action and disease target model configured to generate the predicted mode of action and target diseases.

In some examples, the prediction engine comprises a classifier trained using reduced known cell response profiles, where the reduced known cell response profiles are generated by the generative neural network.

Further examples of methods are described herein. Some example methods include generating a cell response profile for a compound based on input data corresponding to the compound, creating a reduced cell response profile using a generative model generated using known cell response profiles corresponding to tested compounds, and generating predictions for the compound using a comparison between the reduced cell response profile and known reduced cell response profiles generated from the known cell response profiles.

Some methods may further include generating validation information for the predictions using a validation engine configured to extract validation information from reference sources using the predictions.

In some examples, the comparison between the reduced cell response profile and the known reduced cell response profiles uses a classifier trained using the known reduced cell response profiles.

In some examples, the generative neural network includes relationships between the known reduced cell response profiles and one or more of immune response, immune coverage, mode of action, and target diseases of the tested compounds.

Example systems are described herein. Some example systems include a prediction engine comprising a generative neural network including relationships between reduced cell response profiles corresponding to compounds and compound data corresponding to the compounds. The prediction engine may be configured to generate predictions for a compound of interest based on input data corresponding to the compound of interest and to generate compound information based on cell response data. The example systems may further include a validation engine configured to generate validation information corresponding to a compound of interest responsive to receipt of predictions corresponding to the compound of interest from the prediction engine.

In some examples, the prediction engine may further comprise a classifier trained using the reduced cell response profiles as training data.

In some examples, the prediction engine may further comprise a representation analysis module configured to analyze the generative neural network to generate the predictions.

In some examples, the validation engine may be further configured to update the prediction engine using the validation information.

In some examples, the cell response profiles may comprise gene expression data and peptide and protein levels and types.

In some examples, the prediction engine may be configured to generate predictions for the compound of interest by generating a reduced cell response profile corresponding to the compound of interest.

In some examples, the compound of interest may include two or more sub-compounds and generating predictions for the compound of interest may comprise generating a reduced compound cell response profile using reduced cell response profiles corresponding to the two or more sub-compounds.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The description will be more fully understood with reference to the following figures in which components are not drawn to scale, which are presented as various examples of the present disclosure and should not be construed as a complete recitation of the scope of the disclosure, characterized in that.

DETAILED DESCRIPTION

Figure 1:
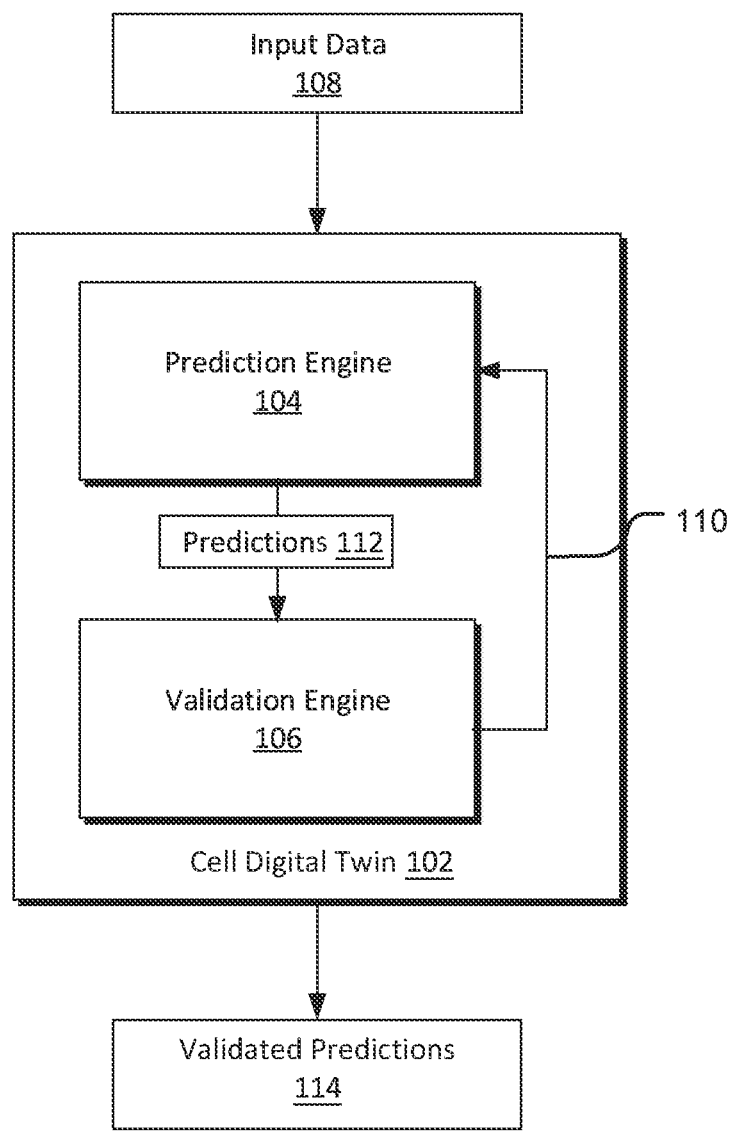
FIG. 1 is a schematic diagram showing implementation of an example system including a cell digital twin.

According to the present disclosure, a system including a cell digital twin or digital replica of a biological cell is disclosed. The system generates predictions for a compound of interest based on cell response data, (e.g., transcriptomic data, a cytokine profile, or a protein profile) from a cell line exposed to the compound, chemical data regarding the structure of the compound, or other data about the compound. The system uses the cell response data to generate predictions, such as, predicted mode of action, predicted target diseases, and/or predicted immune responses. The system may also reference predictions with reference sources to generate validated predictions, e.g., determine likelihood or otherwise rank predication accuracy. Predictions, whether or not validated, can be used to assess whether the compound may be able to treat different conditions and diseases, without having to biologically and iteratively test the compound. The system may also provide new uses for compounds, assisting in both drug and vaccine development.

The cell digital twin may also be used to discover compounds having specific effects on cells. For example, the cell digital twin may receive a desired mechanism or mode of action and return compounds having the same desired mechanism or mode of action. The returned compounds may include compounds that are not chemically similar as the cell analyzed, but may be used to treat the same diseases or conditions.

Cell response data as used herein is meant to encompass gene expression (transcriptomic) data in the form of RNA sequences, microarrays, or other types of transcriptomic data and/or protein or peptide level data in the form of cytokine profiles or other protein or peptide profiles. A cell response profile as used herein is meant to encompass gene expression data and protein or peptide level data. Cell response data or cell response profiles corresponding to a compound as used herein are meant to encompass cell response data or cell response profiles measured or derived from exposing a cell line to the compound.

Input data used herein generally refers to cell response data, as well as compound chemical structures, compound mechanism or mode of action, disease target, immune response, or any gene expression data derived from exposing a biological cell line to a compound. Compound data as used herein is meant to encompass input data corresponding to a tested or known compound, as well as a name or other identifier of a tested or known compound.

Predictions as used herein are meant to encompass one or more of a predicted drug mechanism or mode of action, predicted disease targets, predicted immune response, and predicted immune coverage. Predicted immune response may be presented in term of temporal immune response, trained innate immunity, or adaptive immunity.

Validation information as used herein is meant to encompass one or more of reference detail related to predictions, where the additional or reference detail is derived from reference sources (e.g., databases, papers, literature, etc.) and may include citations to relevant materials including the predictions, a list of similar compounds, a compound safety profile, additional information regarding a compound derived from reference sources, and a validation score approximating strength of the validation information. Validated predictions include one or more predictions and one or more pieces of validation information, which may indicate the likelihood of the predication being accurate.

The cell digital twin as used herein may encompass a software representation of a biological cell that can be used to predict outcomes of experiments involving a biological cell or cell line. The digital cell twin may include models that mathematically mimic biological processes within a biological cell. For example, using input data from a biological cell line exposed to a compound, the cell digital twin provides predictions about biological interactions between the compound and other biological cells (e.g., drug mode of action or immune response), without requiring biological experiments using a biological cell line. Similarly, the cell digital twin can be used to predict a cell response profile of a biological cell at different dosages or combinations of compounds. To this end, the digital cell twin may also include hardware components configured to execute the predictions and optional validations.

For example, the cell digital twin includes a prediction engine to generate compound predictions from cell response data or other input data. The prediction engine includes a generative neural network that ascertains relationships between cell response profiles of known compounds. Known compounds may be, for example, compounds for which data exists regarding the compound's mode of action, target diseases, pathways, or other relevant clinical or biological information. The generative neural network may be trained or generated using cell response profiles of known compounds and, during the training process, may develop a network of reduced representations of cell response data of known compounds. Cell response data may include, for example, transcriptomic data, other gene expression data, pathways in a cell affected by a compound, protein levels and protein types generated by a cell exposed to a compound, peptide levels and peptide types of a cell exposed to a compound, and other data generally measured from a cell or cell line exposed to a compound.

The generative neural network may include reduced cell response profiles. For example, reduced cell response profiles may be represented as vectors with fewer data points than the cell response profiles received as input, retaining only significant data. Proximity of reduced cell response profiles within the generative neural network also may represent closely related compounds or compounds that regulate or affect similar genes within a cell line.

To generate predictions, the generative neural network may generate a reduced cell response profile for a compound of interest based on input data regarding the compound of interest. In some implementations, the predictions may be generated using unsupervised learning and the generative neural network. In other implementations, a classifier or other supervised learning model may be trained using reduced known cell response profiles generated by the generative neural network as training data. The classifier generates predictions based on the reduced cell response profile for the compound of interest.

FIG. 1 shows a high-level implementation of use of an example system including a cell digital twin 102. The cell digital twin generally includes a prediction engine 104 receiving input data 108 correlating to a compound and generating predictions 112 for the compound. The cell digital twin also includes a validation engine 106 receiving predictions 112 from the prediction engine 104 to generate validation information.

Input data 108 may be provided to the cell digital twin 102 as it is measured or obtained from a cell line exposed to a compound. Input data 108 may also be obtained from a storage location by, for example receiving a selection of the input data and a request to retrieve the input data from a computing device. The input data 108 may, in some implementations be sent from one computing device or storage location to a computing device or cluster of computing devices used in implementation of the cell digital twin.

The prediction engine 104 and the validation engine 106 may be implemented in a local computing device, a server, distributed across multiple local computing devices, or may be distributed across several computing devices associated with a network, such as a cloud computing network, LAN, WLAN, or other type of network. A computing device implementing the prediction engine 104 or the validation engine 106 may generally include one or more processors, which may be implemented using, for example, one or more central processing units (CPUs), graphics processing units (GPUs), any number of processor cores, controllers, microcontrollers, and/or other processing circuitry. The prediction engine 104 and the validation engine 106 may be implemented using the same or different computing devices.

Models may be implemented by the prediction engine 104 and the validation engine 106 and may include one or more machine learning models, artificial intelligence models, algorithms, or other functions configured to generate predictions 112 and validation information 114 based on input data 108. Generally, the prediction engine 104 includes a model generated based on cell response profiles corresponding to known or studied compounds. For example, in one implementation, the prediction engine 104 includes a classifier trained using representations of known cell responses generated by a generative neural network also implemented by the prediction engine 104. The validation engine 106 may include a natural language processing model and an image processing model to generate validation information.

Validated predictions 114 may be displayed to a user via a display of a computing device or may be otherwise transmitted from the digital cell twin 102 to the user or another computing device for further use, storage, or display. In some implementations, predictions 112 and validation information may also be stored, displayed, or transmitted.

The example of FIG. 1 shows one example of use of a system including a cell digital twin 102. Input data 108 is obtained regarding a compound of interest. For example, in one implementation, a physical cell line is exposed to a bioactive compound of interest. Input data 108 is collected or measured from the cell line after exposure to the compound of interest. The input data 108 is then transmitted to the prediction engine 104 of the digital cell twin 102.

The prediction engine 104 uses the received input data 108 to generate predictions, such as a predicted mode of action for the compound. The prediction engine 104 generally includes one or more analysis modules that generate a cell response profile for the compound from the input data. For example, analysis modules may generate genetic expression profiles and protein and peptide levels and types for a compound.

The prediction engine 104 generally also includes at least one generative neural network that includes information about cell response profiles corresponding to known compounds. For example, in some implementations, the generative neural network generates a reduced cell response profile from a received cell response profile and compares the received cell response profile to known cell response profiles using the reduced cell response profile. The generative neural network may then retrieve information about the mode of action of the known compounds and extrapolate a predicted mode of action for the compound based on similarities and differences between the cell response profiles of the known compounds and the cell response profile of the compound.

The validation engine 106 analyzes reference sources, such as research, scientific publications, patent applications, video transcripts, databases, drug information databases, and other materials or sources to obtain additional information about known compounds to provide validation information used in generation of validated predictions 114. The cell digital twin 102 may also include a feedback loop 110 between the validation engine 106 and the prediction engine 104, such that the validation engine 106 verifies results generated by the prediction engine 104 and improves accuracy of the prediction engine 104 over time.

The validated predictions 114 may be, for example and without limitation, transmitted to a user computing device, multiple user computing devices, stored on a shared storage system, or used in further calculations or analysis.

Figure 2:
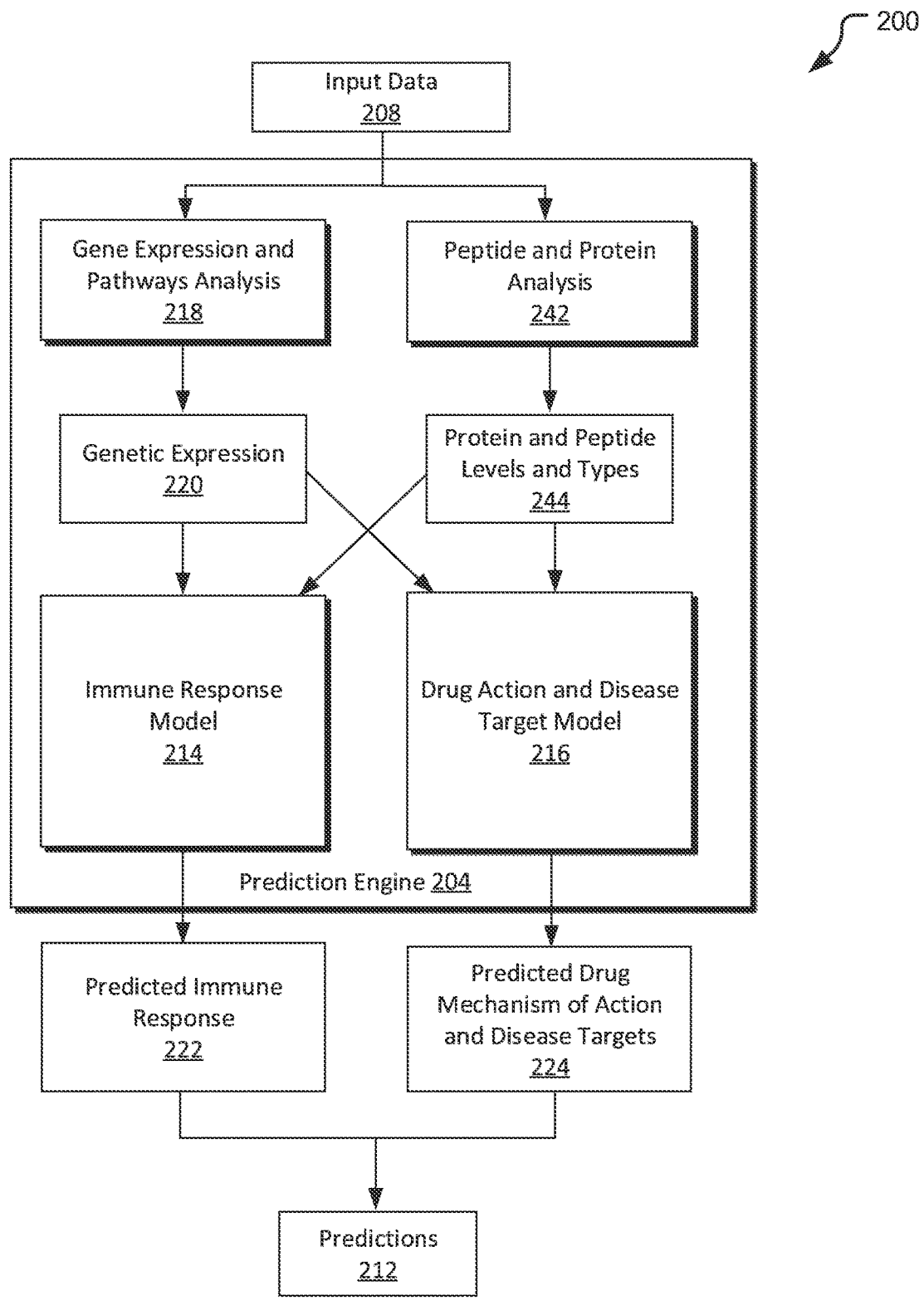
FIG. 2 is a schematic diagram of an example prediction engine of a cell digital twin.

FIG. 2 is a schematic diagram of an example prediction engine 202 including an immune response model 214 and a drug action and disease target model 216. Gene expression and pathways analysis 218 generates genetic expression 220 from input data 208 and peptide and protein analysis 242 generates protein and peptide levels and types 244 from input data 208. The genetic expression 220 and the protein and peptide levels and type 244 together form a cell response profile relayed to the immune response model 214 and the drug action and disease target model 216. The immune response model 214 generates a predicted immune response 222 of the predictions 212 and the drug action and disease target model 216 generates predicted drug mechanism of action and disease targets 224 of the predictions 212. Some implementations of prediction engines may include only an immune response model or only a drug action and disease target model.

Gene expression and pathways analysis 218 may be implemented using a computing device, including any number of cores or processors. Gene expression and pathways analysis 218 may also be implemented using a distributed computing system, a cloud computing environment, or other processing solution. Gene expression and pathways analysis 218 generally receives input data 208 corresponding to a compound and identifies genes affected by the compound as well as pathways targeted by the compound.

Peptide and protein analysis 242 may be implemented using the same or similar hardware and techniques described with respect to gene expressions and pathways analysis 218. Peptide and protein analysis 242 also receives input data 208 and generates protein and peptide levels and types 244. In some implementations, the gene expression and pathways analysis 218 and the peptide and protein analysis 242 are performed using shared hardware such as a computing device or processor.

The immune response model 214 and the drug action and disease target model 216 may each include a generative neural network that generates a reduced representation of a cell response profile including genetic expression 220 and protein and peptide levels and types 244. Further, the immune response model 214 and the drug action and disease target model 216 each include further logic, hardware, software, or models to generate predictions from the reduced cell response profile.

The prediction engine 204 may be implemented using some or all of the hardware and techniques used to implement the prediction engine 104 of FIG. 1. Components of the prediction engine 204 may be implemented on one computing device with one or more processors, multiple computing devices coupled using a network, a cloud computing system, or other combination of computing devices.

As described above, the prediction engine 204 is generally configured to receive input data 208 corresponding to a compound and to generate predictions 212 based on the input data 208. Input data 208 received at the prediction engine 204 is provided as input to both gene expression and pathways analysis 218 and peptide and protein analysis 242. Gene expression and pathways analysis 218 generates genetic expression 220 that includes gene expression data. The peptide and protein analysis module 242 generates protein and peptide levels and types 244, which includes protein and peptide level data. The gene expression and pathways analysis 218 and the peptide and protein analysis 242 generally include formulas, algorithms, or other equations or methods to generate their respective outputs.

Together, the genetic expression 220 and the protein and peptide levels and types 244 form a cell response profile for the compound are each conveyed to both the immune response model 214 and the drug action and disease target model 216. The immune response model 214 uses the received genetic expression 220 and protein and peptide levels and types 244 to generate predicted immune response 222 for the compound. The drug action and disease target model 216 uses the received genetic expression 220 and protein and peptide levels and types 244 to generate predicted drug mechanism of action and disease targets 224 for the compound. The predicted immune response 222 and the predicted drug mechanism of action and disease targets 224 combined form predictions 212. In some implementations, predictions 212 may include additional predictions and the prediction engine 204 may include additional models. In some implementations, predictions 212 may include only predicted immune response 222 or only predicted drug mechanism of action and disease targets 224.

Figure 3:
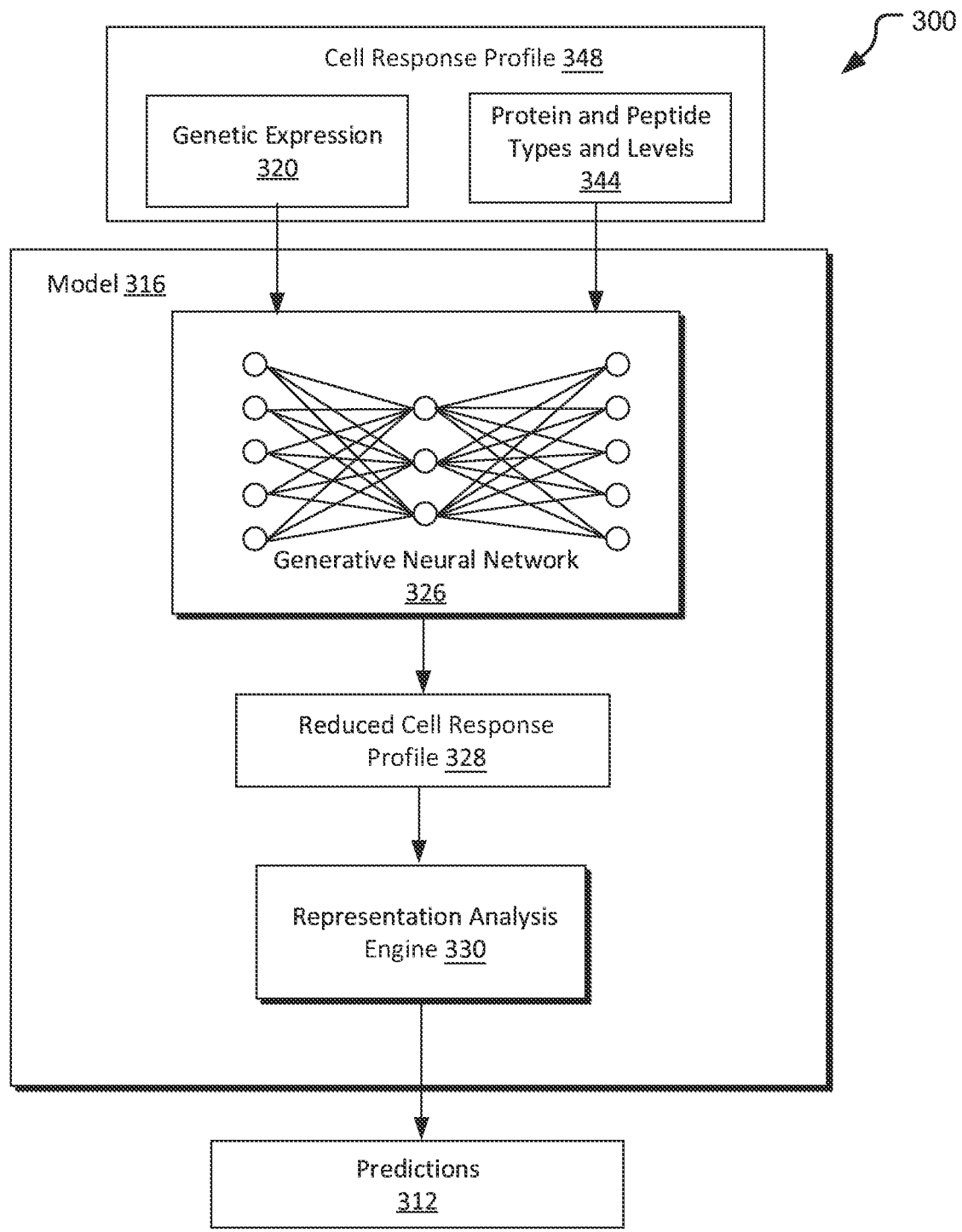
FIG. 3 is a schematic diagram of an example model of a prediction engine of a cell digital twin.

FIG. 3 is a schematic diagram of an example model 316 of a cell digital twin. The model 316 includes a generative neural network 326 that generates a reduced cell response profile 328 from a cell response profile 348. The cell response profile 348 includes genetic expression data 320 and protein and peptide types and levels 344. A representation analysis engine 330 uses the reduced cell response profile 328 to generate predictions 312. The model 316 may implement, for example, the immune response model 214 or the drug action and disease target model 216 of FIG. 2.

The generative neural network 326 may be trained and configured to generate reduced representations 328 from cell response profiles 348. The generative neural network 326 generally uses dimensional reduction to generate the reduced representations 328 and is trained to generate the reduced representations 328 through exposure to known or real cell response profiles. The generative neural network 326 may be implemented, for example, using a generative adversarial network, a variational autoencoder, an adversarial autoencoder, other types of generative networks or models, or combinations of types of generative networks or models.

In some implementations, the generative neural network 326 may be implemented using a generative adversarial network. A generative adversarial network generally includes a generator and a discriminator. The generator and the discriminator may be separate machine learning models or algorithms that receive input from an outside source and feedback from each other to generate a network including representations of cell response data corresponding to known compounds. Different types of generative adversarial networks may be used such as conventional generative adversarial networks or Wasserstein generative adversarial networks.

The generator receives random samples from a distribution as input so that the data generated by the generator generally follows the distribution. The distribution may be, for example, a beta distribution with known parameters, a normal distribution, or other distribution or statistical analysis to represent and evaluate the desired data set. The discriminator receives cell response profiles as input. The cell response profiles are generally correlated to known compounds. The discriminator may also receive compounding information about the known compounds such as mode of action, targets, pathways, immune responses, or other data related to the action of the known compounds. The discriminator may receive and be trained using different types of cell response data. For example, a network produced by the discriminator may include gene expression data and protein and peptide level data.

The cell response profiles and additional input data may be stored at a remote storage location communicatively connected to the generative adversarial network or may be local to the generative adversarial network. Additionally, the input data may be distributed across several data storage locations. In some implementations, additional logic, processing, or models may process the cell response data to standardize, format, or otherwise prepare the cell response profiles for input into the generative adversarial network.

The generative adversarial network generally functions as an adversarial iterative feedback process between the generator and the discriminator, with feedback between the generator and the discriminator improving the performance of both the generator and the discriminator. In each iteration of the generative adversarial network, the generator receives a random sample from the distribution and generates a fake cell response profile based on the random sample and any information the generator has about characteristics of a cell response profile. The discriminator receives the fake cell response profile from the generator and a cell response profile from the input data and determines which cell response profile is real. The discriminator then returns information about its decision to the generator. In the next iteration, the generator has more information about what a cell response profile should look like. Over time, the discriminator develops a network of cell response profiles and the generator generates more realistic cell response profiles. After the generative adversarial network is trained, the neural network generated by the discriminator can receive cell response profiles 348 and generate reduced cell response profiles 328.

Collaboration between the generator and the discriminator also enables dimensionality reduction of the cell response profiles used in training of the generative adversarial network. Dimensionality reduction provides simplified or reduced representations of the cell response profiles emphasizing important distinctions between the profiles while other, less relevant data drops out of the profiles or is condensed. In some implementations, the system may use these representations of the cell response profiles to obtain data about dosing of compounds and combinations of compounds using the cell digital twin instead of or in addition to exposure of cell lines to different doses or combinations of compounds. For example, a generative neural network 326 generated by the discriminator could be interrogated to obtain reduced cell response profiles for two known compounds. The reduced cell response profiles of the known compounds could be algebraically or arithmetically combined to create an additional cell response profile representing the combination of the compounds. The additional cell response profile may then be provided as input to the prediction engine to obtain a compound prediction for the combination of the compounds.

In another implementation, the generative neural network 326 may be implemented using a variational autoencoder. In other implementations the generative neural network 326 may be implemented using an adversarial autoencoder. Both a variational autoencoder and an adversarial autoencoder may be generated using real cell response data and may generate dimensionally reduced representations of cell response profiles. Once trained, the variational autoencoder and the adversarial autoencoder are both configured to receive a cell response 348 and to generate a reduced cell response profile 328.

The representation analysis engine 330 may include supervised learning models configured to receive the reduced cell response profile 328 to generate predictions 312 or may include unsupervised learning models configured to receive the reduced cell response profile 328 to generate predictions 312.

Where the representation analysis engine 330 includes supervised learning models, the network of the generative neural network 326, reduced cell response profiles generated by the generative neural network, and other information may be used to train the models. For example, in one implementation, the representation analysis engine 330 includes a classifier trained using the reduced cell response profiles along with information about the compounds corresponding to the reduced cell response profiles as labeled observations. Other supervised learning models may include, for example, decision trees, random forests, or other types of classifiers.

For example, the representation analysis engine 330 may be implemented including a random forest, decision tree, or Bayesian network trained using labeled observations provided by the generative neural network 326. The representation analysis engine 330 may also be implemented by several machine learning models working in conjunction to generate a predictions 312 from a reduced cell response profile 328.

In other implementations, the representation analysis engine 330 includes unsupervised learning models that may, for example, use the generative neural network 326 to generate predictions 312 based on a reduced cell response profile 328. For example, clustering or other techniques may be used on the generative neural network 326 by the representation analysis engine 330 to generate predictions 312.

In some implementations, the representation analysis engine 330 may be used to analyze reduced cell response profiles from one or more sub-compounds making up a compound to obtain predictions for the compound. The representation analysis engine 330 may obtain reduced representations for the sub-compounds by interrogating a model or models within the generative neural network 326. The representation analysis engine 330 may then combine the reduced representations of the sub-compounds to obtain a reduced representation for the compound and use the reduced representation for the compound to generate predictions 312.

For example, predictions may be generated for a new compound "C" including some amount of a known compound "A" and a known compound "B." Interrogating the generative neural network 326, reduced dimensionality cell responses may be obtained representing the response of cell lines to compound A and compound B. To predict the response of a cell line to compound C, the reduced dimensionality cell responses may be added and input into the representation analysis engine as reduced cell response profile 328. Accordingly, compound predictions for compounds including different amounts of compounds A and B may be obtained without actually creating the compounds and measuring cell response to exposure to the compounds.

In an example use of the model 316, the cell response profile 348 includes genetic expression 320 and protein and peptide types and levels 344. The cell response profile 348 is input to the generative neural network 326 to produce a reduced cell response profile 328. The representation analysis engine 330 generates the predictions based on similarities between the reduced cell response profile 328 and nodes within the generative neural network 326 using supervised or unsupervised learning. For example, the representation analysis engine 330 may identify a cluster of known compounds with similar transcriptomic data and may interpolate a mode of action for the compound of interest based on known modes of actions of the known compounds within the identified cluster. Other machine learning algorithms, alone or in combination, such as a random forest, Bayes classifier, or neural network may be used by the representation analysis engine 330 to identify similar known compounds and to interpolate information about the compound of interest through a comparison with known compounds.

In some implementations, the model 316 may be used to generate compound information (e.g., identification of compounds) for desired mechanisms of action, disease targets, or immune response. For example, the model 316 may be used to identify related compounds using the generative neural network 326.

Figure 4:
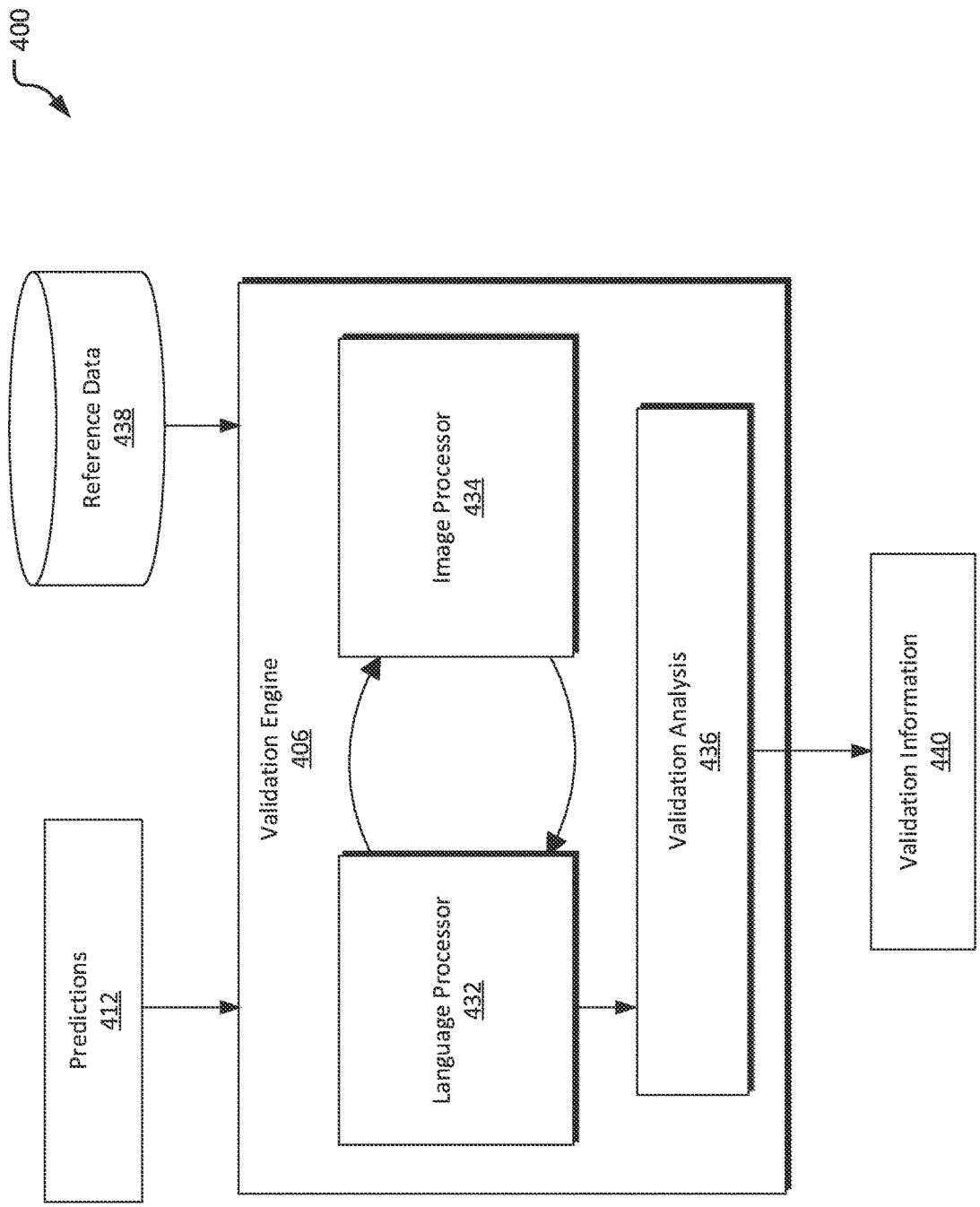
FIG. 4 is a schematic diagram of an example validation engine of a cell digital twin.

FIG. 4 is a schematic diagram of an example validation engine 406 of a cell digital twin. The validation engine 406 includes a language processor 432 and an image processor 434 that receive predictions 412 as input and draw on reference data 438. Reference data 438 may be processed by the language processor 432 or the image processor 434 depending on the format of the reference data 438. Validation analysis 436 receives extracted information from the language processor 432 to generate validation information 440.

The validation engine 406 may be implemented using some or all of the hardware and techniques described in the implementation of the validation engine 106 of FIG. 1. The validation engine 406 may be coupled to storage including reference data 438 and may include a network interface, such as a wireless interface, to access additional reference data, update existing reference data, or perform other functions. The validation engine 406 is generally configured or trained to extract relevant information from the reference data, which may include documents, publications, or other sources of information about bioactive compounds.

Reference data 438 may include publications, documents, images, or other source data regarding bioactive compounds from any reference sources. In one example, the reference data 438 is gathered from publicly available, private, and/or subscription databases or other sources. The reference data 438 generally includes documents, such as text articles, publications, or other video, audio, or other documentations including information about bioactive compounds. The reference data 438 also may include experimental data or drug information data. The information may include mode of action, targets, pathways, target diseases, dosing information, experimental data, and other data regarding bioactive compounds. The reference data 438 may be gathered and stored on storage of the validation engine 406 and may be updated with new documentation periodically. In some implementations, the reference data 438 may be also or alternatively accessed on an as-needed basis by the prediction engine validation engine 406 using a network (e.g., the Internet).

The validation engine 406 may include language processor 432, such as, a natural language processor or sequential language understanding deep neural network, configured to receive documents regarding known compounds and to tag specific features of the publications such as mode of action, pathways, targets, target diseases, genetic response, immune response, or other data. The language processor 432 may be trained to identify text in multiple languages or may include a translator. The validation engine 406 utilizes the reference data to add information to the predictions, which may generate a validated prediction or indicate that a prediction is likely incorrect. The validation information 440 may be returned to the prediction engine to improve the prediction engine's performance over time.

An image processor 434 may be used by the language processor 432 to extract additional information from the reference sources. For example, graphs, charts, tables, and some document formats may not be immediately parsed by the language processor 432. When the language processor 432 recognizes that there is content within a reference that the language processor 432 cannot parse, the language processor 432 may pass the reference to the image processor 434 to obtain text from the images. The image processor may be implemented using machine learning or artificial intelligence models, such as a convolutional neural network.

Validation analysis 436 may include various components to format data received from the language processor 432. For example, validation analysis 436 may aggregate data extracted by the language processor 432 to provide summaries of available information. Validation analysis 436 may also include physical computing or software components that calculate a validation score from data received from the language processor 432. For example, a validation score may be calculated as a percentage of references that mention a particular mode of action (or other compound prediction) of all of the references mentioning a compound.

In an example use of the validation engine 406, predictions 412 are transmitted to the validation engine. The language processor 432 and the image processor 434 may search the reference data 318 for references including compounds with similar modes of action, pathways, targets, etc. Validation analysis 436 may then format retrieved or extracted data and calculate or otherwise determine a validation score to include in the validation information 440. The validation information 440 is generally added to predictions 412 to generate validated predictions that are displayed using some device or interface, transmitted for display or storage, or otherwise stored or conveyed to a user. In some implementations, the compound validation information 440 or other information obtained by validation engine 406 may be returned to the prediction engine to increase accuracy of the prediction engine.

Figure 5:
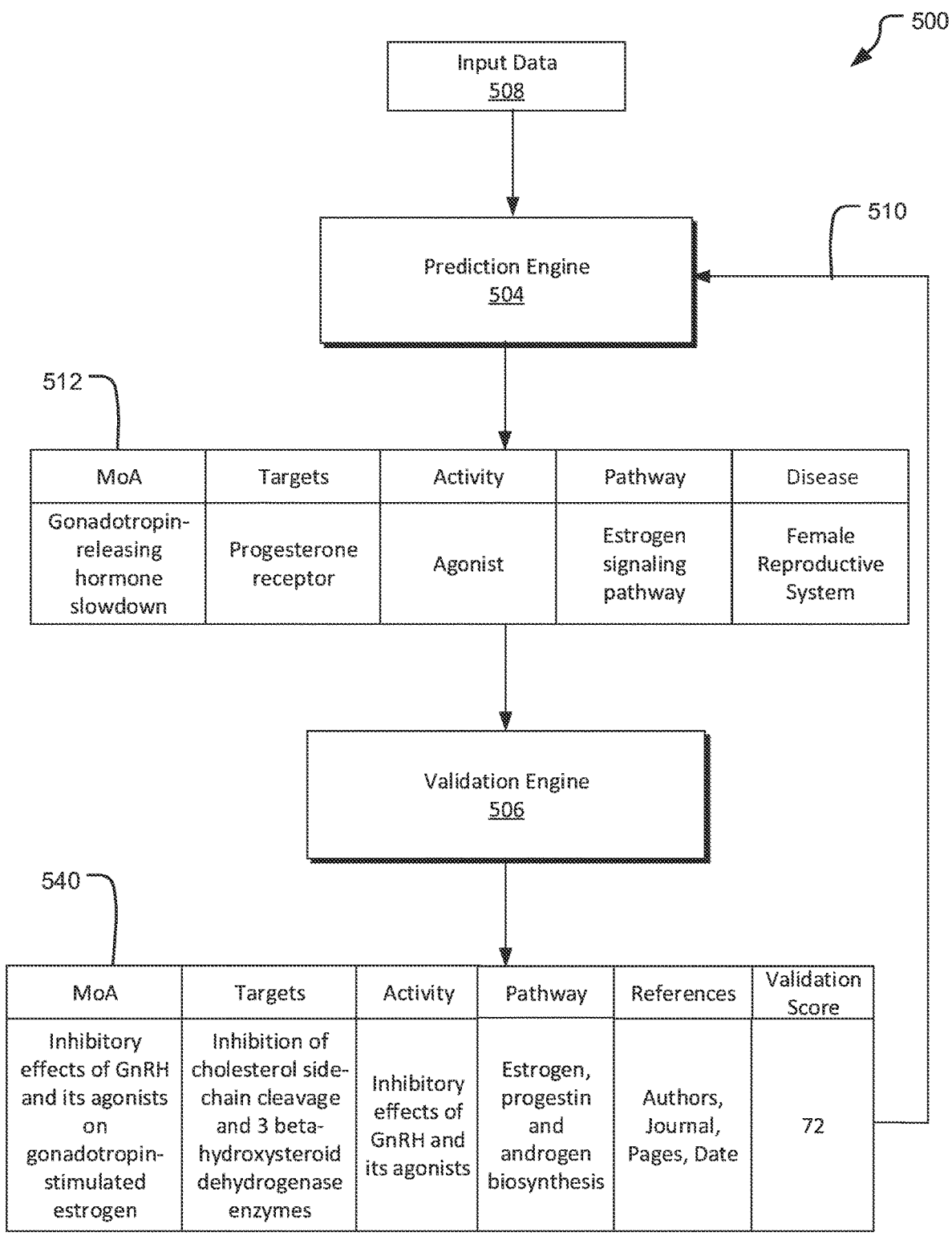
FIG. 5 is a schematic diagram of an example system including a cell digital twin.

FIG. 5 is a schematic diagram of an example cell digital twin 500. The prediction engine 504 receives input data 508 and generates predictions 512. The validation engine 506 generates validation information 540 based on the predictions 512. In a feedback loop 510, the validation engine 506 transmits the validation information 540 to the prediction engine 504 to improve performance of the prediction engine 504.

The prediction engine 504 receives input data 508 and generates predictions 512. For example, the prediction engine 504 may generate predictions 512 using similar methods as those described above with respect to prediction engine 204 of FIG. 2. The predictions 512 include mode of action, targets, activity, pathways, and system affected by the compound correlating to the input data 508. The predictions 512 shown are exemplary and other predictions may include additional information, such as predicted immune response measured by, for example t-cell response or phenotypic data such as fever. Further, for some compounds, multiple target diseases or systems may be included for one compound.

The predictions 512 are provided to the validation engine 506. The validation engine 506 uses the predictions 512 and reference data to generate validation information 540. For example, the validation engine 506 may generate validation information 540 using similar methods as those described above with respect to the validation engine 406 of FIG. 4. The validation information 540 includes mode of action, targets, activity, and pathway corresponding to the data provided in the predictions 512. In some implementations, the validation information 540 may include information for each prediction of the predictions 512. In some implementations, the validation information 540 may include additional information described in references but not included in the predictions 512. The validation information 540 also includes references, which generally includes citations to articles, publications, locations in a database, or other documents including extracted information used to generate the validation information 540. The validation information 540 also includes a validation score, which may approximate the strength of the validation information 540.

Additionally, in some implementations, the validation engine 506 may provide the validation information 540 as feedback to the prediction engine 504 so that models within the prediction engine 504 become more accurate and/or efficient over time. For example, the mode of action, targets, activity, and pathways of the validation information 540 may be returned to the prediction engine 504 via feedback loop 510 and used to update a classifier, generative neural network, or other models within the prediction engine.

Figure 6:
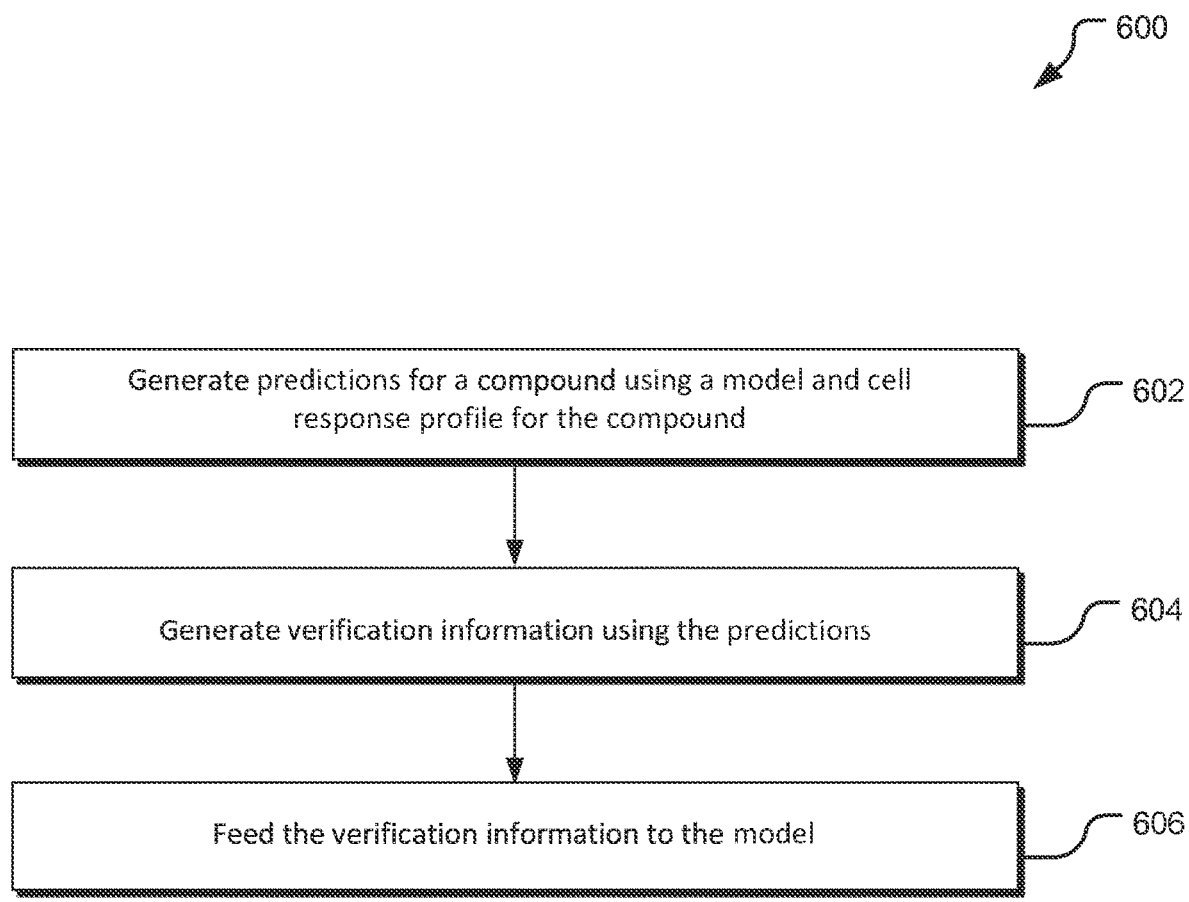
FIG. 6 is a flow diagram of steps for generating predictions corresponding to a compound.

FIG. 6 is a flow diagram of steps or operations 600 for generating a compound prediction using a bioactive compound analysis system. A cell response profile is generated for a compound using input data corresponding to the compound. The cell response profile may be obtained using analysis modules configured to receive input data corresponding to the compound and generate a full cell response. In some implementations, the input data may be a subset of the full cell response profile.

A first generating operation 602 generates predictions for the compound using a model and the cell response profile for the compound. The first generating operation 602 may include generating one or more subsets of predictions. For example, in the prediction engine 204 of FIG. 2, an immune response model 216 and a drug action and disease target model 216 each generate predictions that are aggregated to form predictions 212. The models may receive the cell response and, using a generative neural network (e.g., generative neural network 326 of FIG. 3) may generate a reduced representation of the cell response profile. A representation analysis engine 330 uses the reduced cell response profile to generate a subset of predictions (e.g., predicted immune response 222 and predicted drug mechanism of action and disease targets 224) optionally can be combined to form predictions for the compound. For example, predictions may include mode of action, targets, activity, pathways, and disease, as shown in predictions 512 of FIG. 5.

A second generating operation 604 generates validation information using the predictions. The second generating operation 604 may include receiving predictions and searching reference sources for keywords or other indicators related to the predictions. For example, a language processor, image processor, or other types of processors may search through reference sources to locate reference data including publications, documents, and other sources to locate information similar to the predictions or demonstrating the accuracy of the prediction. For example, verification information 540 in FIG. 5 shows a similar, but more detailed mode of action as the mode of action predicted in predictions 512. In some implementations, a validation analysis module may aggregate data tagged or extracted by processors and format the data for inclusion in the validation information. The validation information may also include citations to references that were used to generate the validation information and a validation score roughly reflecting the strength of the validation information.

A feedback operation 606 feeds the validation information to the model. For example, the mode of action, targets, activity, and pathways of the validation information may be returned to one or more models of a prediction engine using a feedback loop and used to update a classifier, generative neural network, or other models within the prediction engine.

Figure 7:
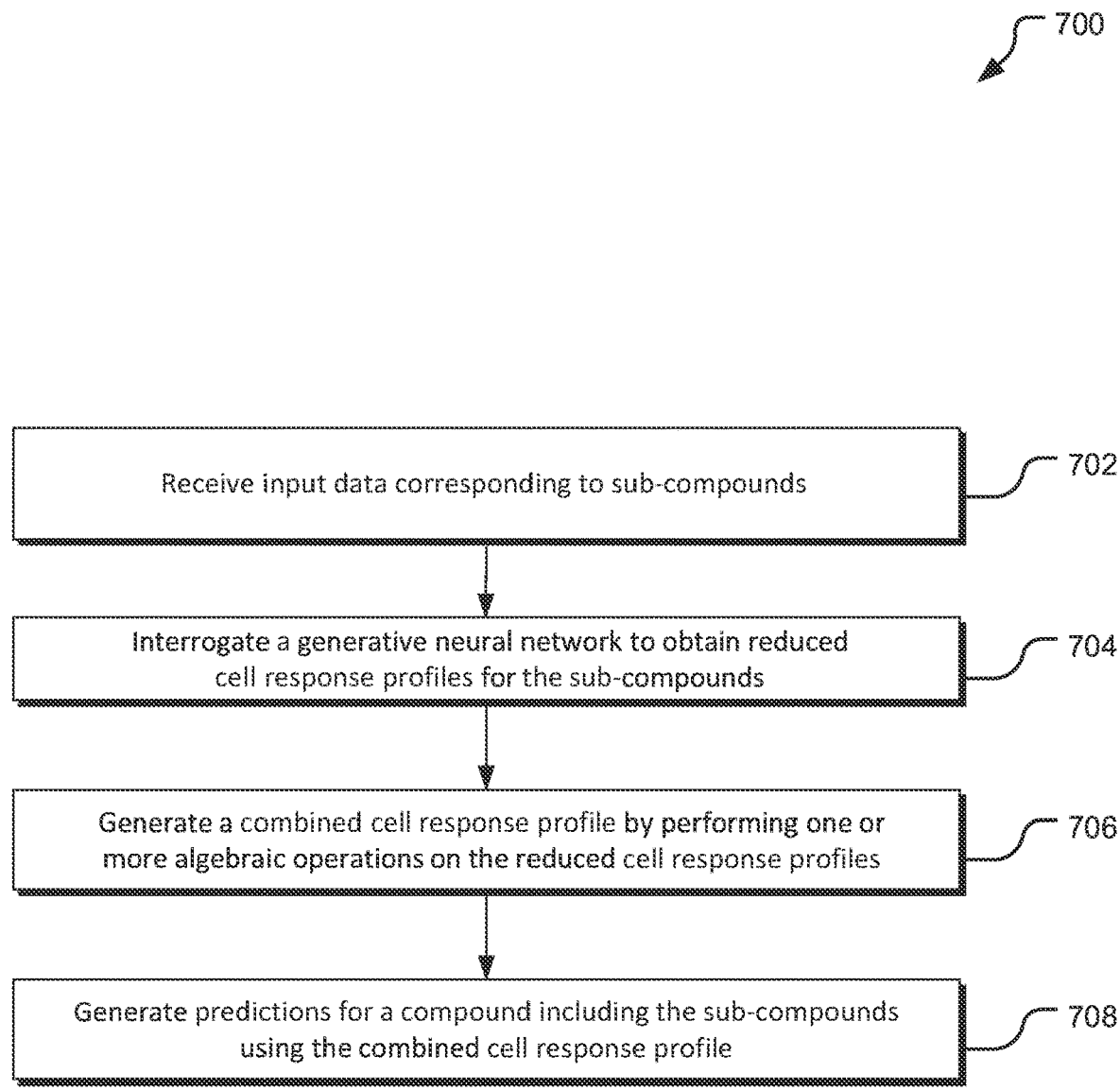
FIG. 7 is a flow diagram of steps for generating predictions for a compound including one or more sub-compounds.

FIG. 7 is a flow diagram of steps or operations 700 for generating a compound prediction using reduced representations of cell responses of sub-compounds included in a compound. The operations 700 may be implemented, for example, to determine predicted response of a cell line exposed to different doses or combinations of compounds. A receiving operation 702 receives input data corresponding to sub-compounds.

An interrogating operation 704 interrogates a generative neural network to obtain reduced cell response profiles for the sub-compounds. In some implementations, a generative neural network may generate the reduced cell response profiles based on cell response profiles generated by analysis models from the input data. In other implementations, the input data may be directly used to retrieve a pre-constructed reduced cell response profile from a neural network. The reduced cell response profiles may, for example, collapse numbers indicating the expression of co-expressed genes into a single number, simplifying the cell response profiles while maintaining critical information within the profiles.

A first generating operation 706 generates a combined cell response profile by performing one or more algebraic operations on the reduced cell response profiles. For example, reduced cell response profiles may be scaled up through multiplication, scaled down through division, added, or subtracted to simulate different dosages or combinations of compounds. The reduced cell response profiles may be manipulated linearly but retain non-linear properties of full cell response profiles.

A second generating operation 708 generates predictions by using the combined cell response profile. The second generating operation 708 generates the predicted response in the same way as the second generating operation 604. In some implementations, there may be differences between how the prediction engine processes a combined cell response profile versus cell response generated through exposure of a cell line or other tissue to a compound. For example, combined cell responses are already dimensionally reduced. In some implementations, a reference validation model or language processing model may be used to generate additional information for inclusion in the predicted response or compound prediction. The predicted response may provide researchers with information regarding how different dosages of compounds or combinations of compounds behave in a biological system before actually creating the compounds and measuring responses.

Figure 8:
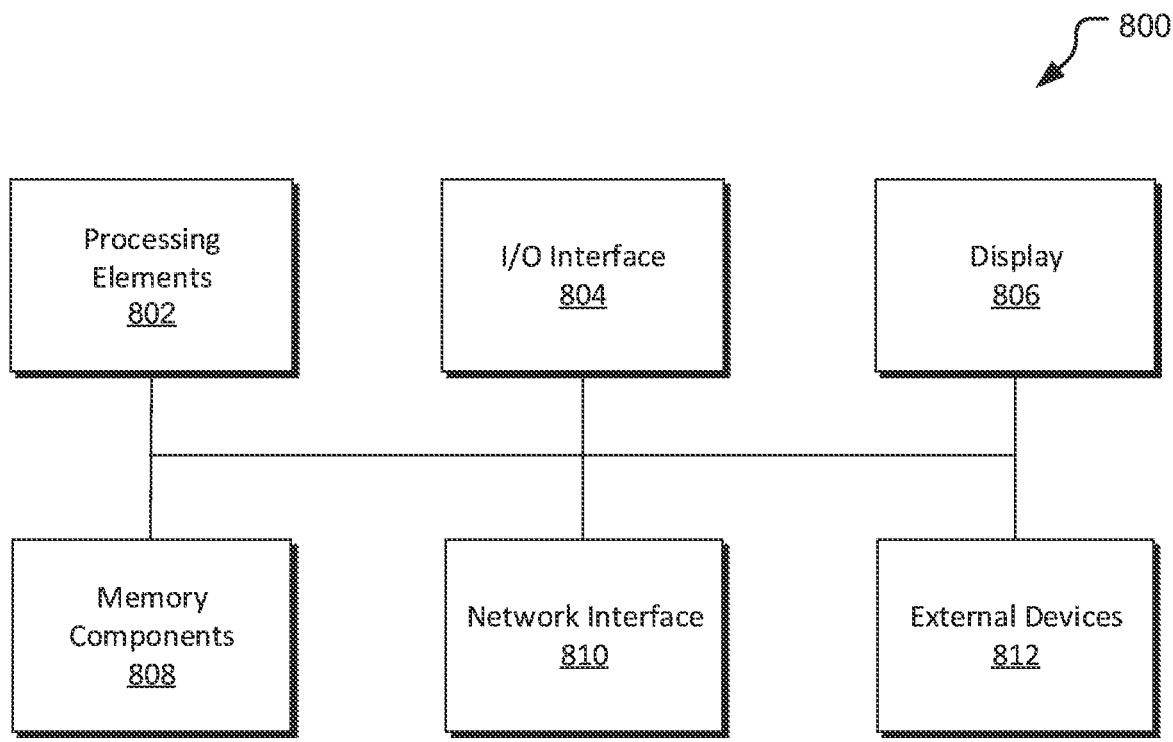
FIG. 8 is a schematic diagram of an example computer system for implementing various embodiments in the examples described herein.

FIG. 8 is a schematic diagram of an example computer system for implementing various embodiments in the examples described herein. A computer system 800 may be used to implement the prediction engine 104 (in FIG. 1) or integrated into one or more components of the system. For example, the prediction engine 104 and the validation engine 106 may be implemented on a computing device that may include one or more of the components of the computer system 800 shown in FIG. 8. The computer system 800 is used to implement or execute one or more of the components or operations disclosed in FIGS. 1-7. In FIG. 8, the computer system 800 may include one or more processing elements 802, an input/output interface 804, a display 806, one or more memory components 808, a network interface 810, and one or more external devices 812. Each of the various components may be in communication with one another through one or more buses, communication networks, such as wired or wireless networks.

The processing element 802 may be any type of electronic device capable of processing, receiving, and/or transmitting instructions. For example, the processing element 802 may be a central processing unit, microprocessor, processor, or microcontroller. Additionally, it should be noted that some components of the computer 800 may be controlled by a first processor and other components may be controlled by a second processor, where the first and second processors may or may not be in communication with each other.

The memory components 808 are used by the computer 800 to store instructions for the processing element 802, as well as store data, such as reference data (e.g., 438 in FIG. 4), and the like. The memory components 808 may be, for example, magneto-optical storage, read-only memory, random access memory, erasable programmable memory, flash memory, or a combination of one or more types of memory components.

The display 806 provides visual feedback to a user, such as a display of a user device to display the predictions 112 (FIG. 1). Optionally, the display 806 may act as an input element to enable a user to control, manipulate, and calibrate various components of the system as described in the present disclosure. The display 806 may be a liquid crystal display, plasma display, organic light-emitting diode display, and/or other suitable display. In embodiments where the display 806 is used as an input, the display may include one or more touch or input sensors, such as capacitive touch sensors, a resistive grid, or the like.

The I/O interface 804 allows a user to enter data into the computer 800, as well as provides an input/output for the computer 800 to communicate with other devices or services (e.g., components in FIG. 1). The I/O interface 804 can include one or more input buttons, touch pads, and so on.

The network interface 810 provides communication to and from the computer 800 to other devices. For example, the network interface 810 may allow the prediction engine 204 (FIG. 1) to communicate with a user device or other devices used to collect and store input data 108 (FIG. 1) through a communication network. The network interface 810 includes one or more communication protocols, such as, but not limited to WiFi, Ethernet, Bluetooth, and so on. The network interface 810 may also include one or more hard-wired components, such as a Universal Serial Bus (USB) cable, or the like. The configuration of the network interface 810 depends on the types of communication desired and may be modified to communicate via WiFi, Bluetooth, and so on.

The external devices 812 are one or more devices that can be used to provide various inputs to the computing device 800, e.g., mouse, microphone, keyboard, trackpad, or the like. The external devices 812 may be local or remote and may vary as desired. In some examples, the external devices 812 may also include one or more additional sensors.

The foregoing description has a broad application. For example, while examples disclosed herein may focus on central communication system, it should be appreciated that the concepts disclosed herein may equally apply to other systems, such as a distributed, central or decentralized system, or a cloud system. For example, the components in the prediction engine 204 (FIG. 2) or the validation engine 406 (FIG. 4) may reside on a server in a client/server system, on a user mobile device, or on any device on the network and operate in a decentralized manner. One or more components of systems described herein may also reside in a controller virtual machine (VM) or a hypervisor in a VM computing environment. Accordingly, the disclosure is meant only to provide examples of various systems and methods and is not intended to suggest that the scope of the disclosure, including the claims, is limited to these examples.

The technology described herein may be implemented as logical operations and/or modules in one or more systems. The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A computer implemented method comprising:
receiving, at a cell digital twin, input data corresponding to data previously acquired from a biological cell line previously exposed to a compound of interest;
generating, by the cell digital twin, predictions about biological interactions between the compound of interest and biological cells based on the input data, wherein:
the cell digital twin comprises a prediction engine, the prediction engine comprising a generative neural network trained using known cell response profiles corresponding to tested compounds, and
the prediction engine generates biological interaction predictions between the compound of interest and the biological cells using the generative neural network, the biological interaction predictions including one or more of predicted immune response, predicted immune coverage, predicted mode of action, or predicted drug action and target diseases;
generating, by a validation engine, validated predictions using the biological interaction predictions generated by the cell digital twin, wherein:
the validation engine generates validation information by parsing one or more images of one or more references, processing text of the one or more references, and searching the processed text and the parsed images of the one or more references for one or more of the predicted immune response, predicted immune coverage, predicted mode of action, or predicted drug action and target diseases, and the validated predictions include the biological interaction predictions and the validation information; and updating the prediction engine by providing the validated predictions to the prediction engine using a feedback loop between the validation engine and the prediction engine.

2. The computer implemented method of claim 1, further comprising:

generating a cell response profile for the compound of interest based on the input data; and generating a dimensionally reduced cell response profile using the generative neural network, wherein the predictions are generated using a comparison between the dimensionally reduced cell response profile and known cell response profiles generated from the known cell response profiles.

3. The computer implemented method of claim 1, wherein the validated predictions include a validation score reflecting strength of the validation information.

4. The computer implemented method of claim 1, wherein the cell response profile comprises one or more of genetic expression data and peptide and protein levels and types.

5. The computer implemented method of claim 1, wherein the generative neural network includes dimensionally reduced known cell response profiles generated from the known cell response profiles, wherein the known cell response profiles represent genetic expression data and peptide and protein levels and types corresponding to known compounds.

6. The computer implemented method of claim 1, wherein the prediction engine comprises an immune response model configured to generate the predicted immune response and a drug action and disease target model configured to generate at least one of the predicted mode of action or the predicted drug and target diseases.

7. The computer implemented method of claim 1, wherein the prediction engine further comprises a classifier trained using dimensionally reduced known cell response profiles, wherein the method further comprises:

generating, by the generative neural network, the dimensionally reduced known cell response profiles.

8. The computer implemented method of claim 1, wherein the generative neural network is a generative adversarial network, the generative neural network including a generator machine learning model and a discriminator machine learning model.

9. A computer implemented method comprising:

generating a cell response profile including genetic expression data and protein and peptide data for a compound based on input data corresponding to data previously acquired from a biological cell line previously exposed to the compound;

creating a dimensionally reduced cell response profile representing the genetic expression data and the protein and peptide data using a generative neural network trained using known cell response profiles corresponding to tested compounds;

generating biological interaction predictions, the biological interaction predictions predicting interactions between the compound and biological cells using a comparison between the dimensionally reduced cell response profile and known dimensionally reduced cell response profiles generated from the known cell response profiles, the biological interaction predictions including one or more of predicted immune response, predicted immune coverage, predicted mode of action, or predicted drug interaction and target diseases;

generating validated predictions including the biological interaction predictions and validation information generated by parsing one or more images of one or more references, processing text of the one or more references, and searching the processed text and the parsed images of the one or more references for one or more of the predicted immune response, predicted immune coverage, predicted mode of action, or predicted drug interaction and target diseases; and updating one or more models used to generate the biological interaction predictions by providing the validated predictions to the one or more models.

10. The computer implemented method of claim 9, wherein the comparison between the dimensionally reduced cell response profile and the known dimensionally reduced cell response profiles uses a classifier trained using the known dimensionally reduced cell response profiles.

11. The computer implemented method of claim 9, wherein the generative neural network includes relationships between the known dimensionally reduced cell response profiles and one or more of immune response, immune coverage, mode of action, and target diseases of the tested compounds.

12. The computer implemented method of claim 9, wherein the generative neural network is a generative adversarial network, the generative neural network including a generator machine learning model and a discriminator machine learning model.

13. A system comprising:

one or more processors;

memory encoding instructions that, when executed by the one or more processors, are configured to implement a prediction engine comprising a generative neural network, the generative neural network including dimensionally reduced cell response profiles corresponding to cell response data of compounds, wherein the prediction engine:

is configured to generate a dimensionally reduced cell response profile corresponding to a compound of interest based on input data corresponding to data previously acquired from a biological cell line previously exposed to the compound of interest; and is configured to generate biological interaction predictions predicting interactions between the compound of interest and biological cells based on a comparison between the dimensionally reduced cell response profile corresponding to the compound of interest and the dimensionally reduced cell response profiles of the generative neural network, the biological interaction predictions including one or more of predicted immune response, predicted immune coverage, predicted mode of action, or predicted drug action and target diseases; and memory encoding instructions that, when executed by the one or more processors, implement a validation engine configured to generate validated predictions using the biological interaction predictions generated by the prediction engine, wherein:

the validation engine is configured to generate validation information by parsing one or more images of one or more references, processing text of the one or more references, and searching the processed text and the parsed images of the one or more references for one or more of the predicted immune response, predicted immune coverage, predicted mode of action, or predicted drug action and target disease, the validated predictions include the biological interaction predictions and the validation information, and the validation engine updates the prediction engine by providing the validated predictions to the prediction engine using a feedback loop between the validation engine and the prediction engine.

14. The system of claim 13, wherein the prediction engine further comprises a classifier trained using the dimensionally reduced cell response profiles as training data.

15. The system of claim 13, wherein the prediction engine generates the predictions using the generative neural network.

16. The system of claim 13, wherein the cell response profiles comprise gene expression data and peptide and protein levels and types.

17. The system of claim 13, wherein the compound of interest includes two or more sub-compounds and wherein generating predictions for the compound of interest comprises generating the dimensionally reduced cell response profile corresponding to the compound of interest using dimensionally reduced cell response profiles corresponding to the two or more sub-compounds.

18. The system of claim 13, wherein the generative neural network is a generative adversarial network, the generative neural network including a generator machine learning model and a discriminator machine learning model.

* * * * *